United States Patent
Stamp et al.

(10) Patent No.: US 8,187,226 B2
(45) Date of Patent: May 29, 2012

(54) AUTOINJECTOR

(75) Inventors: Kevin Stamp, Sheffield (GB); Charles Ian Cleathero, Leicestershire (GB)

(73) Assignee: The Medical House Limited (GB)

( * ) Notice: Subject to any disclaimer, the term of this patent is extended or adjusted under 35 U.S.C. 154(b) by 61 days.

(21) Appl. No.: 12/530,107

(22) PCT Filed: Mar. 4, 2008

(86) PCT No.: PCT/GB2008/000741
§ 371 (c)(1),
(2), (4) Date: Sep. 4, 2009

(87) PCT Pub. No.: WO2008/107670
PCT Pub. Date: Sep. 12, 2008

(65) Prior Publication Data
US 2010/0130930 A1  May 27, 2010

(30) Foreign Application Priority Data
Mar. 7, 2007 (GB) .................................. 0704351.6

(51) Int. Cl.
*A61M 5/20* (2006.01)
(52) U.S. Cl. ........................................ 604/135; 604/167
(58) Field of Classification Search .................. 604/135, 604/167, 156
See application file for complete search history.

(56) References Cited

U.S. PATENT DOCUMENTS

| | | | |
|---|---|---|---|
| 60,917 A | 1/1867 | Brown | |
| 3,702,608 A * | 11/1972 | Tibbs | 604/136 |
| 3,756,242 A | 9/1973 | Coss | |

(Continued)

FOREIGN PATENT DOCUMENTS

DE 102004060146 8/2005

(Continued)

OTHER PUBLICATIONS

Official Action for U.S. Patent Application No. 12/161,776, mailed Oct. 6, 2010, 21 pages.

(Continued)

*Primary Examiner* — Jackie Ho
*Assistant Examiner* — Gerald Landry, II
(74) *Attorney, Agent, or Firm* — Sheridan Ross P.C.

(57) ABSTRACT

An autoinjector comprising an outer housing in which is mounted a syringe, the autoinjector further comprising an inner housing intermediate the outer housing and the syringe and an energy source in communication with said inner housing, wherein the inner housing is moveable by the energy source between three positions, namely a first position in. which the inner housing is in communication with the barrel such that, in use, the plunger and barrel are moveable axially so as to move at least part of said needle out of the outer housing; a second position in which the inner housing is in communication with the plunger but not the barrel such that, in use, said plunger is moveable axially into said barrel so as to expel medicament through the needle; and a third position in which the inner housing is in communication with neither the plunger nor the barrel such that, in use, the plunger and barrel are able to retract in order to retract the needle into the outer housing, characterized in that the plunger includes biasing means for axially biasing the barrel, before activation of the energy source, to a position forward of the part of the inner housing which acts on the barrel in said first position.

19 Claims, 17 Drawing Sheets

U.S. PATENT DOCUMENTS

| | | | |
|---|---|---|---|
| 3,797,489 | A | 3/1974 | Sarnoff |
| 3,811,442 | A | 5/1974 | Maroth |
| 4,617,016 | A | 10/1986 | Blomberg |
| 4,913,699 | A | 4/1990 | Parsons |
| 4,923,447 | A | 5/1990 | Morgan |
| 4,958,622 | A | 9/1990 | Selenke |
| 4,976,724 | A | 12/1990 | Nieto et al. |
| 5,024,656 | A | 6/1991 | Gasaway et al. |
| 5,042,977 | A | 8/1991 | Bechtold et al. |
| 5,078,698 | A | 1/1992 | Stiehl et al. |
| 5,167,632 | A | 12/1992 | Eid et al. |
| 5,211,625 | A | 5/1993 | Sakurai et al. |
| 5,300,030 | A | 4/1994 | Crossman et al. |
| 5,320,609 | A | 6/1994 | Haber et al. |
| 5,478,316 | A | 12/1995 | Bitdinger et al. |
| 5,568,261 | A | 10/1996 | Wakai et al. |
| 5,599,309 | A * | 2/1997 | Marshall et al. ............ 604/136 |
| 5,634,906 | A | 6/1997 | Haber et al. |
| 5,658,261 | A | 8/1997 | Neer et al. |
| 5,681,291 | A | 10/1997 | Galli |
| 5,779,675 | A | 7/1998 | Reilly et al. |
| 5,779,677 | A | 7/1998 | Frezza |
| 6,203,530 | B1 | 3/2001 | Stewart, Sr. |
| 6,210,369 | B1 | 4/2001 | Wilmot et al. |
| 6,264,629 | B1 | 7/2001 | Landau |
| 6,270,479 | B1 * | 8/2001 | Bergens et al. ............ 604/156 |
| 6,280,421 | B1 | 8/2001 | Kirchhofer et al. |
| 6,544,234 | B1 | 4/2003 | Gabriel |
| 6,605,072 | B2 | 8/2003 | Struys et al. |
| 6,607,510 | B2 | 8/2003 | Landau |
| 6,620,137 | B2 | 9/2003 | Kirchhofer et al. |
| 6,632,198 | B2 | 10/2003 | Caizza |
| 6,656,163 | B1 | 12/2003 | Marshall et al. |
| 6,689,093 | B2 | 2/2004 | Landau |
| 6,702,608 | B2 | 3/2004 | Brennan, Jr. |
| 6,752,781 | B2 | 6/2004 | Landau et al. |
| 6,981,499 | B2 | 1/2006 | Anderson et al. |
| 7,156,823 | B2 | 1/2007 | Landau et al. |
| 7,976,499 | B2 * | 7/2011 | Grunhut et al. ............ 604/110 |
| 2001/0005781 | A1 | 6/2001 | Bergens et al. |
| 2001/0049496 | A1 * | 12/2001 | Kirchhofer et al. ......... 604/154 |
| 2003/0105430 | A1 | 6/2003 | Lavi et al. |
| 2003/0236502 | A1 | 12/2003 | De La Serna et al. |
| 2005/0027255 | A1 | 2/2005 | Lavi et al. |
| 2005/0165349 | A1 | 7/2005 | Stamp et al. |
| 2005/0165360 | A1 | 7/2005 | Stamp |
| 2006/0100589 | A1 | 5/2006 | Lin |
| 2007/0173770 | A1 | 7/2007 | Stamp |
| 2007/0265568 | A1 | 11/2007 | Tsals et al. |
| 2008/0228143 | A1 | 9/2008 | Stamp |
| 2009/0012471 | A1 | 1/2009 | Harrison |
| 2010/0069846 | A1 | 3/2010 | Stamp |

FOREIGN PATENT DOCUMENTS

| | | |
|---|---|---|
| EP | 0453212 | 10/1991 |
| EP | 0518416 | 12/1992 |
| EP | 0740942 | 11/1996 |
| EP | 0864335 | 9/1998 |
| EP | 1323447 | 7/2003 |
| EP | 1323477 | 7/2003 |
| EP | 2080532 | 7/2009 |
| GB | 886444 | 1/1962 |
| GB | 2388033 A | 11/2003 |
| GB | 2396298 | 6/2004 |
| GB | 2397767 A | 8/2004 |
| GB | 2410188 | 7/2005 |
| GB | 2414398 | 11/2005 |
| WO | WO 94/21316 A | 9/1994 |
| WO | WO 99/22792 | 5/1999 |
| WO | WO 00/09186 | 2/2000 |
| WO | WO 01/93926 | 12/2001 |
| WO | WO 02/070051 | 9/2002 |
| WO | WO 03/097133 | 11/2003 |
| WO | WO 03/099358 | 12/2003 |
| WO | WO 2005/009515 A | 2/2005 |
| WO | WO 2005/009520 A | 2/2005 |
| WO | WO 2005/070481 A | 8/2005 |
| WO | WO 2005/097252 | 10/2005 |
| WO | WO 2005/115507 | 12/2005 |
| WO | WO 2005/115512 A | 12/2005 |
| WO | WO 2006/052737 A | 5/2006 |
| WO | WO 2006/106291 | 10/2006 |
| WO | WO 2006/106295 | 10/2006 |
| WO | WO 2007/083115 | 7/2007 |
| WO | WO 2007/132353 | 11/2007 |
| WO | WO 2008/075033 | 6/2008 |
| WO | WO 2008/107670 | 9/2008 |
| WO | WO 2010/026414 A | 3/2010 |

OTHER PUBLICATIONS

Authorized Officer Reinbold, International Preliminary Report on Patentability for International (PCT) Patent Application No. PCT/GB2005/000223, mailed Jan. 23, 2006, 13 pages.

Authorized Officer Reinbold, Written Opinion for International (PCT) Patent Application No. PCT/GB2005/000223, mailed Jun. 22, 2005, 7 pages.

UK Search Report for Application No. GB0602411.1, dated Apr. 7, 2006, 4 pages.

Corrected Search Report under Section 17 for Application No. GB0620163.6, dated Nov. 24, 2006, 1 page.

International Search Report for International (PCT) Patent Application No. PCT/GB2007/000141, mailed May 5, 2007, 2 pages.

Authorized Officer Bjorklund, Written Opinon for International (PCT) Patent Application No. PCT/GB2007/000141, mailed May 5, 2007, 7 pages.

Authorized Officer Mulhausen, International Preliminary Report on Patentability for International (PCT) Patent Application No. PCT/GB2007/000141, mailed Jul. 29, 2008, 8 pages.

Official Action for U.S. Appl. No. 10/767,859, mailed Feb. 24, 2006, 8 pages.

Official Action for U.S. Appl. No. 10/767,859, mailed Sep. 12, 2006, 10 pages.

Official Action for U.S. Appl. No. 10/767,859, mailed Jun. 5, 2007, 8 pages.

Official Action for U.S. Appl. No. 10/767,859, mailed Dec. 28, 2007, 8 pages.

Official Action for U.S. Appl. No. 10/767,860, mailed Mar. 14, 2006, 8 pages.

Official Action for U.S. Appl. No. 10/767,860, mailed Aug. 22, 2006, 8 pages.

Official Action for U.S. Appl. No. 10/767,860, mailed Dec. 15, 2006, 3 pages.

Official Action for U.S. Appl. No. 10/767,860, mailed Apr. 10, 2007, 7 pages.

Official Action for U.S. Appl. No. 10/767,860, mailed Sep. 24, 2007.

Official Action for U.S. Appl. No. 10/767,860, mailed Jan. 11, 2008, 8 pages.

Official Action for U.S. Appl. No. 10/767,860, mailed Jun. 12, 2008, 6 pages.

Advisory Action for U.S. Appl. No. 10/767,860, mailed Sep. 5, 2008, 3 pages.

Official Action for U.S. Appl. No. 10/767,860, mailed Dec. 2, 2008, 5 pages.

Interview Summary for U.S. Appl. No. 10/767,860, mailed Feb. 2, 2009, 4 pages.

Notice of Allowance for U.S. Appl. No. 10/767,860, mailed Aug. 27, 2009, 8 pages.

Restriction Requirement for U.S. Appl. No. 11/387,645, mailed May 28, 2009, 7 pages.

Official Action for U.S. Appl. No. 10/597,379, mailed Jul. 31, 2008, 12 pages.

Official Action for U.S. Appl. No. 10/597,379, mailed Feb. 23, 2009, 9 pages.

Official Action for U.S. Appl. No. 11/387,645, mailed Sep. 17, 2010, 29 pages.

Formalities Officer Sulis, Communication pursuant to Rule 114(2) EPC for European Patent Application No. 07704923.4, mailed Sep. 29, 2010, 9 pages.

U.S. Appl. No. 10/597,379, Stamp et al.

U.S. Appl. No. 12/161,776, Stamp et al.

International Search Report issued by the European Patent Office on Dec. 23, 2008, for International Application No. PCT/GB2008/000741, pp. 1-8.
Written Opinion of the International Searching Authority issued by the European Patent Office on Dec. 23, 2008, for International Application No. PCT/GB2008/000741, pp. 1-15.
International Preliminary Report on Patentability issued by the International Bureau of WIPO on Sep. 17, 2009, pp. 1-13.
Search Report issued by the UK Intellectual Property Office on Jul. 1, 2008, for Application No. GB0804021.4, pp. 1-4.
Search Report issued by the UK Intellectual Property Office on Jun. 7, 2007, for Application No. GB0704351.6, pp. 1-4.
U.S. Appl. No. 12/601,220, filed Nov. 20, 2009, Stamp et al.
Authorized Officer Reinbold, International Search Report issued by the European Patent Office on Mar. 19, 2008 for International Application No. PCT/GB2007/004870, 3 pages.
Authorized Officer Reinbold, Written Opinion issued by the European Patent Office on Mar. 19, 2008 for International Application No. PCT/GB2007/004870, 7 pages.
Authorized Officer Mulhausen, International Preliminary Report on Patentability issued on Jun. 24, 2009 for International Application No. PCT/GB2007/004870, 8 pages.
Official Action for U.S. Appl. No. 11/387,645, mailed Feb. 11, 2011, 29 pages.
Notice of Allowance for U.S. Appl. No. 10/597,379, mailed Sep. 2, 2009, 11 pages.
Official Action for U.S. Appl. No. 12/161,776, mailed May 11, 2011, 11 pages.
International Search Report issued by the European Patent Office on May 19, 2010, for International Application No. PCT/GB2009/051716.
Official Action for U.S. Appl. No. 13/189,286, mailed Jan. 4, 2012, 9 pages.
Restriction Requirement for U.S. Appl. No. 12/623,960, mailed Jan. 5, 2012, 6 pages.
Official Action for U.S. Appl. No. 12/623,960, mailed Mar. 5, 2012, 11 pages.

* cited by examiner

AUTOINJECTOR

CROSS REFERENCE TO RELATED APPLICATIONS

This application is a national stage application under 35 U.S.C. 371 of PCT Application No. PCT/GB2008/000741 having an international filing date of 4 Mar. 2008, which designated the United States, which PCT application claimed the benefit of Great Britain Application No. 0704351.6 filed 7 Mar. 2007, the entire disclosure of each of which is hereby incorporated herein by reference.

This invention relates to the field of autoinjectors for the administration of liquid medication.

BACKGROUND

An autoinjector is an automatic injection device designed to facilitate delivery of a dose of medicament to a patient through a hypodermic needle, the injection usually being administered by the patient themselves. An autoinjector works, for example, by delivering an injection automatically upon actuation by the patient pressing a button, moving a lever or part of a housing etc. This is in contrast to a conventional manual syringe where the patient themselves needs to directly depress a plunger into a barrel containing medicament in order to effect the injection. The terms "autoinjector" and "injection device" are used interchangeably in the following description.

An autoinjector is described in our international patent application published under number WO 2005/070481. Some of the reference numerals in the present application correspond with the equivalent components in the device described in WO 2005/070481. This device requires that the needle is moved axially so that it can appear beyond the end of the nozzle for the duration of the injection, after which the needle retracts automatically, so that it is never in sight of the user. The device also requires that the plunger is moved axially so that medicament is ejected. The overall complexity of the autoinjector is significantly reduced by both of these requirements being effected by one component, namely an inner housing (illustrated in FIG. 1 of the present application) and the device has the significant advantage that it can be built around a conventional or standard syringe presentation.

The injection device of WO 2005/070481 is designed to be used in conjunction with a standard drug presentation e.g. a syringe comprising a needle, barrel preloaded with medicament and a plunger. There is a significant commercial advantage in being able to use a standard syringe, which will have been subjected to numerous clinical trials, drug stability studies and regulatory approval. Any modification to the standard syringe may require further trials and approval, adding delay and expense. The present invention is relevant to any injection device for use in conjunction with a syringe (whether preloaded or not and whether single-use or reusable), not only the injection device described in WO 2005/070481.

In the known device described in patent application no WO 2005/070481, the syringe is supported within the injection device by a barrel or syringe holder 9. The syringe holder 9 comprises an elongate housing which closely surrounds the glass barrel of the syringe. The annular flange 90 at the rear of the syringe barrel rests on a barrel seat 91 at the rear of the syringe holder 9. The annular flange 90 at the rear of the syringe barrel is often referred to as a "finger flange" because, during a conventional (manual) injection using a syringe, the user's index and middle fingers rest naturally in front of the "finger flange" in order to provide the necessary resistance to allow depression of the plunger by the thumb to deliver the medicament. The barrel seat 91 preferably prevents forward axial movement of the syringe with respect to the syringe holder so that, in use, the syringe barrel and the syringe holder move axially together as one unit.

The inner housing 7 shown in FIG. 1 includes rear tags 7A which can flex radially into and out of contact with the plunger of the syringe and front tags 7B which can flex radially into and out of contact with the finger flange of the syringe barrel.

In use, as described in WO 2005/070481, there are three stages of delivering an injection. Before delivering an injection (referring to FIG. 2 of the present application), the end cap 15 is pulled off, taking the rigid needle cover 17 (if present) and rubber needle sheath with it. In the first stage of delivering an injection, as shown in FIG. 3 of the present application, the tags 7B at the forward end of the inner housing 7 are in contact with the syringe barrel 90, which is pushed axially forward (taking the syringe holder 9 with it), so that the needle 10, which is fixed to the front end of the barrel, moves in the direction indicated by the arrow so that eventually it protrudes beyond the nozzle 11 at the front of the device. Forward travel of the barrel and syringe holder is limited when a surface 9A of the syringe holder reaches an endstop 11A inside the nozzle or front housing 11.

Referring now to FIG. 4, the second stage of the injection is the delivery of the medicament wherein the tags 7A at the rear of the inner housing 7 depress the plunger 8 into the barrel of the syringe. During this stage, the barrel of the syringe is held axially stationary, by abutment of the annular "finger" flange 90 against the barrel seat 91, which results in the barrel being placed in tension as the plunger pushes the non-compressible liquid medicament towards the forward end of the barrel. This tension is undesirable in a glass barrel, which may become damaged or broken, especially if the medicament comprises a particularly viscous liquid which requires greater force to expel it from the syringe via the needle. Viscous medicaments are desirable in certain applications, where the use of a sustained-release viscous medicament reduces the frequency that an injection is required. The undesirable tension on the barrel during injection can be reduced by using an alternative syringe holder 100 which is shown in FIG. 5 and discussed in our UK patent application number 0620163.6. This type of syringe holder supports the barrel at its front end, using for example radially-flexible fingers 108 which have gripping means on the interior surface thereof.

In the third stage of the injection (not illustrated in the present application but shown in WO 2005/070481), once the medicament has been delivered and the inner housing 7 is no longer in contact with the barrel or plunger of the syringe, the secondary spring 12 pushes the syringe holder (and hence the syringe contained therein) axially rearwardly so as to retract the syringe back into the housing so that the used needle is concealed from view.

FIG. 6 shows the device from GB0620163.6, in its storage condition. Note that the flange 90 of the barrel is forward of the front tags 7B of the inner housing 7. Whilst the endcap 15 is in place, none of the internal components of the device can move axially relative to one another.

When the endcap 15 and needle sheath 17 are removed so that the device is ready for use, it is possible that the syringe will have a tendency to move slightly axially with respect to the outer housing and the inner housing 7. This undesired axial movement could be as a result of "bounce-back" caused by the sudden release of the needle sheath from the needle, or could depend upon the orientation in which the user is holding the device, for example.

This undesired axial movement of the syringe could be prevented by storing the tags 7B in a radially-inward position, i.e. already abutting flange 90 so that it is impossible for the syringe to move rearwardly with respect to the inner housing 7. However, this solution is undesirable because, after storage for a prolonged period of time, it is possible that the plastic tags 7B will acquire "memory" of their radially-inward position such that, during operation of the device, they are not capable of springing radially-outwardly when required to be out of engagement with the syringe barrel (i.e. during the third stage described above).

The performance of the radially-flexible tags 7B during delivery of an injection is optimised by storing them in a radially-outward position (as illustrated in FIG. 6) so that they can be temporarily forced inwardly into contact with the flange 90 when required to move the syringe and its attached needle forward for delivery of an injection, after which they can easily spring back into the radially-outward position (of which they have acquired "memory") after injection when it is desired for the syringe to retract fully into the housing. However, storage of the tags 7B in a radially-outward position means that there is nothing to prevent the undesired axial movement mentioned above when the endcap 15 and needle sheath 17 are removed.

If the undesired axial movement is rearward such that the flange 90 of the barrel comes to rest in a position rearward of the tags 7B, it will not be possible for the device to operate properly because the tags 7B will be unable to engage with the flange in order to move the syringe axially forward as is necessary during the first stage of the injection described above. The failure of the device to operate properly would only become apparent upon actuation of the injection causing uncertainty for the patient and risk to health resulting from incomplete or no dose of medicament being delivered.

A second disadvantage of the prior art arises due to variations in the initial absolute axial position of the rear flange of the plunger from one syringe to the next. The rear flange of the plunger needs to be engaged by the rear tags of the inner housing in order to deliver an injection. These variations in initial axial position could, for example, be caused by manufacturing tolerances, variations in the filling of the syringe with medicament, variations in the volume of the gas bubble inside the syringe, changes in atmospheric pressure (for example if the device is transported by airfreight) etc. These slight variations may affect the volume of the dose of medicament being delivered. The dose of medicament to be delivered is determined by the extent of the axial movement of the plunger into the syringe barrel, which in turn is controlled by the relative positioning of the tags 7A, 7B on the inner housing 7. For a given axial distance traveled by the inner housing (and the rear tags thereof), the actual dose of medicament delivered may vary slightly depending upon the absolute axial starting position of the plunger. This problem is particularly relevant in devices which are designed to deliver a partial dose (e.g. half or quarter) of a full syringe, compared with devices which are designed to deliver a full dose (i.e. completely emptying the syringe). The absolute axial starting position of the plunger may therefore be of importance in maintaining the accuracy of the actual dose of medicament delivered.

SUMMARY OF THE INVENTION

According to a first aspect of the present invention, there is provided an autoinjector comprising an outer housing in which is mounted a syringe comprising a barrel for holding a volume of medicament,
a needle at one end of the barrel and
a plunger axially-moveable in the barrel, the autoinjector further comprising an inner housing intermediate the outer housing and the syringe and an energy source in communication with said inner housing,
wherein the inner housing is moveable by the energy source between three positions, namely
  a first position in which the inner housing is in communication with the barrel such that, in use, the plunger and barrel are moveable axially so as to move at least part of said needle out of the outer housing;
  a second position in which the inner housing is in communication with the plunger but not the barrel such that, in use, said plunger is moveable axially into said barrel so as to expel medicament through the needle; and
  a third position in which the inner housing is in communication with neither the plunger nor the barrel such that, in use, the plunger and barrel are able to retract in order to retract the needle into the outer housing,
characterised in that the autoinjector includes biasing means for axially biasing the barrel, before activation of the energy source, to a position forward of the part of the inner housing which acts on the barrel in said first position.

Preferably, the biasing means acts on said plunger of the syringe and the incompressible nature of the liquid medicament in the syringe transmits the biasing force to the barrel.

In one embodiment, said biasing means comprises a compression spring held between the outer housing and the plunger. Preferably said compression spring is integrally-formed with said plunger. In a preferred form, said compression spring is provided with a rear flange for abutment with a part of said outer housing.

In another embodiment, the biasing means is associated with the front end of said inner housing, located in the axial path of the barrel. Usually, the biasing means is not strong enough to resist a forward axial force provided by said energy source in communication with said inner housing. The biasing means may be one or more radially-flexible legs integrally-formed with said inner housing.

In an alternative embodiment, said biasing means comprises a chamber containing a piston in a shear thickening fluid which, upon activation of said energy source, is capable of transmitting forward axial force from said energy source to the plunger and a compression spring held between the outer housing and said piston.

According to a second aspect of the present invention, there is provided an autoinjector comprising an outer housing in which is mounted a syringe comprising a barrel for holding a volume of medicament,
a needle at one end of the barrel and
a plunger axially-moveable in the barrel,
the autoinjector further comprising an inner housing intermediate the outer housing and the syringe and an energy source in communication with said inner housing,
wherein the inner housing is moveable by the energy source between three positions, namely
  a first position in which the inner housing is in communication with the barrel such that, in use, the plunger and barrel are moveable axially so as to move at least part of said needle out of the outer housing;
  a second position in which the inner housing is in communication with the plunger but not the barrel such that, in use, said plunger is moveable axially into said barrel so as to expel medicament through the needle; and a third position in which the inner housing is in communication with neither the plunger nor the barrel such that, in use, the plunger and barrel are able to retract in order to retract the needle into the outer housing, characterised in that the autoinjector further comprises means associated with a rear flange of said plunger providing a plurality of axial positions at which it is possible for said inner housing to engage said plunger in said second position.

The means providing a plurality of axial positions is associated with the rear flange of the plunger because it is the rear flange of the plunger which is "picked up" by the inner housing in the second position to depress the plunger into the syringe barrel.

In one embodiment, the means associated with said rear flange of the plunger comprises a chamber containing a piston in a shear thickening fluid which, upon activation of said energy source, is capable of transmitting forward axial force from said energy source to the plunger and a compression spring held between the outer housing and said piston.

In an alternative embodiment, the means associated with said rear flange of the plunger comprises a ratchet cap providing an axial range of engagement points for said inner housing in said second position.

Preferably, the autoinjector is a single-use autoinjector. The simple construction of the autoinjector makes it very appropriate for applications such as emergency use for injecting a large population to control a pandemic, where a large number of cost-effective disposable autoinjectors are required. A single-use autoinjector also provides a very convenient means for patients to administer their own injections, even if lacking in dexterity and/or clinical experience.

Typically, the energy source, for example a coiled spring, is capable of moving said plunger axially in the barrel to deliver an injection in less than 30 seconds.

Preferably, the syringe is axially moveable in said housing and is biased so that the needle is normally wholly inside said housing, wherein before injection the syringe is movable axially so as to move at least a part of said needle out of the housing and wherein after injection, the syringe is able to retract in order to retract said part of said needle into the housing. The concealment of the needle both before and after injection makes the autoinjector particularly suitable where the patient has any aversion to injection by needle. Concealment of the needle both before and after injection also eliminates the risk of needle-stick injury.

Further features of the invention are defined in the appended claims.

BRIEF DESCRIPTION OF THE DRAWINGS

Preferred embodiments of the present invention will now be more particularly described, by way of example only, with reference to the accompanying drawings in which.

DETAILED DESCRIPTION

Throughout the description and claims of this specification, the words "comprise" and "contain" and variations of the words, for example "comprising" and "comprises", means "including but not limited to", and is not intended to (and does not) exclude other components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Throughout the following description, reference to a "forward" direction means the direction which is towards the patient when the injection device is in use. The "forward" end of the injection device is the end nearest the patient's skin when the device is in use. Similarly, reference to a "rearward" direction means the direction which is away from the patient and the "rearward" end of the device is the end furthest from the patient's skin when the injection device is in use.

The "plunger" does not necessarily (but may) include any elastomeric stopper or the like which seals the chamber containing liquid medicament.

Features, integers, characteristics or groups described in conjunction with a particular aspect, embodiment or example of the invention are to be understood to be applicable to any other aspect, embodiment or example described herein unless incompatible therewith.

Figure 1:
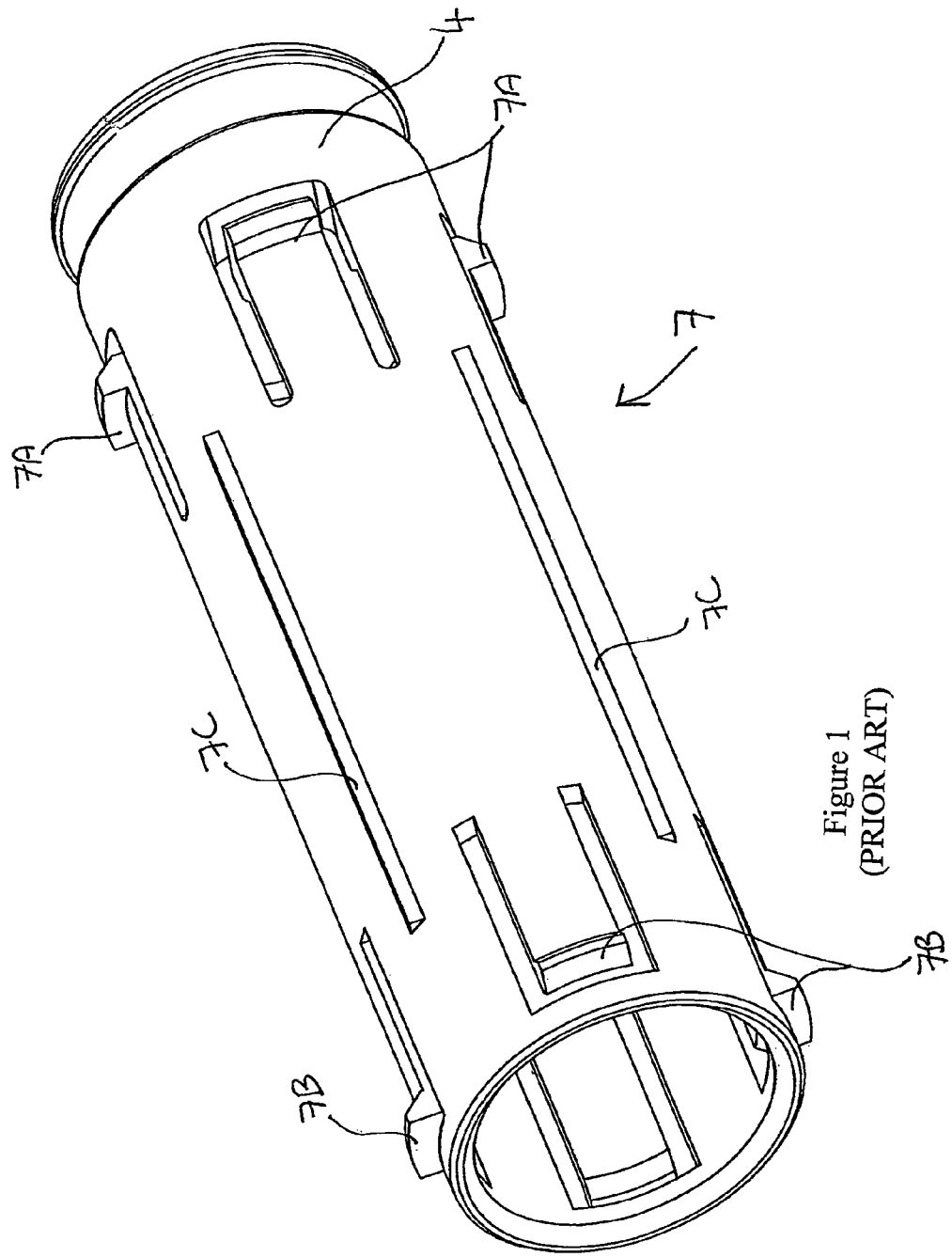
FIG. 1 (PRIOR ART) is a perspective view of the inner housing from WO 2005/070481.
Figure 2:
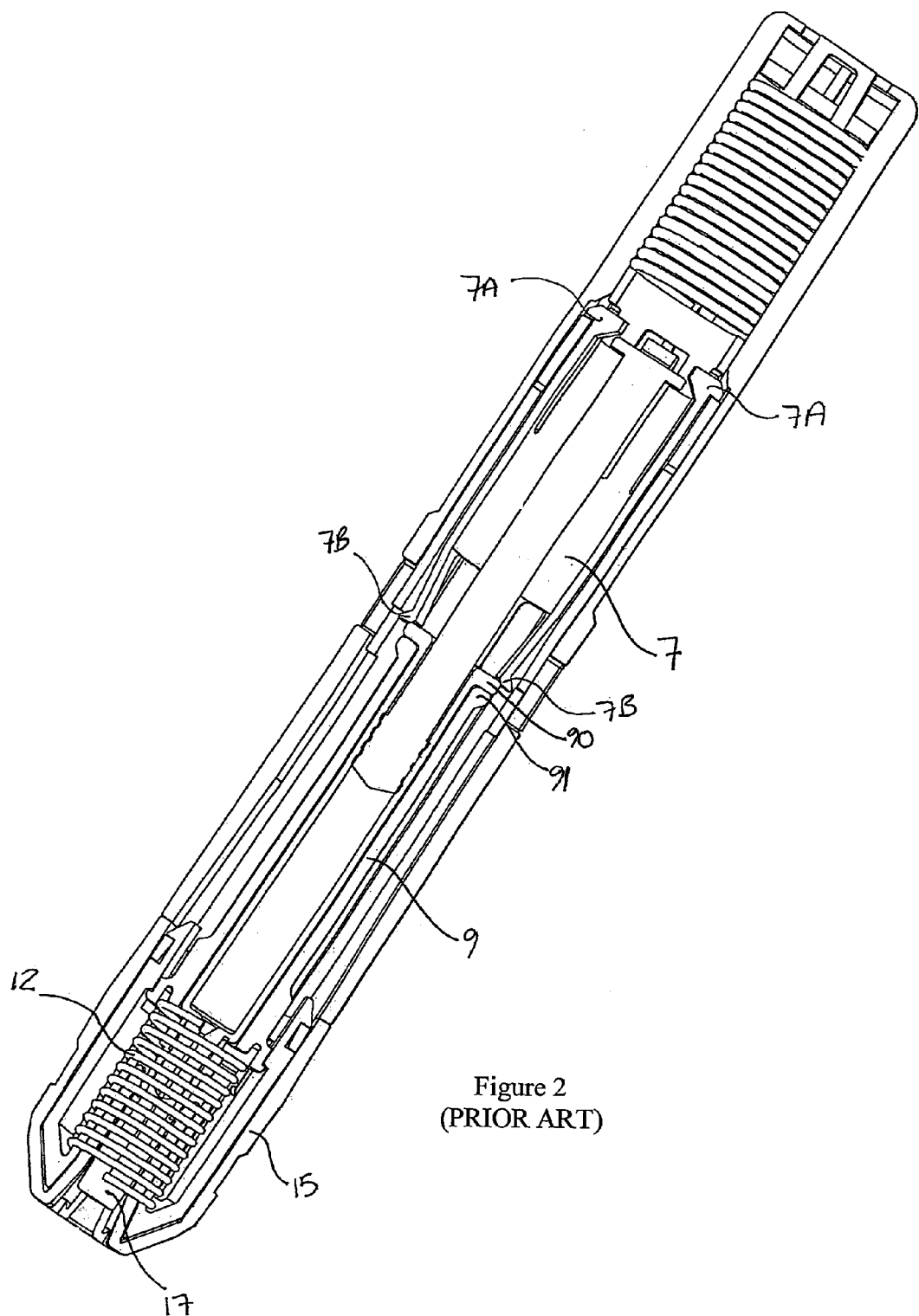
FIG. 2 (PRIOR ART) is a perspective view of a known injection device.
Figure 3:
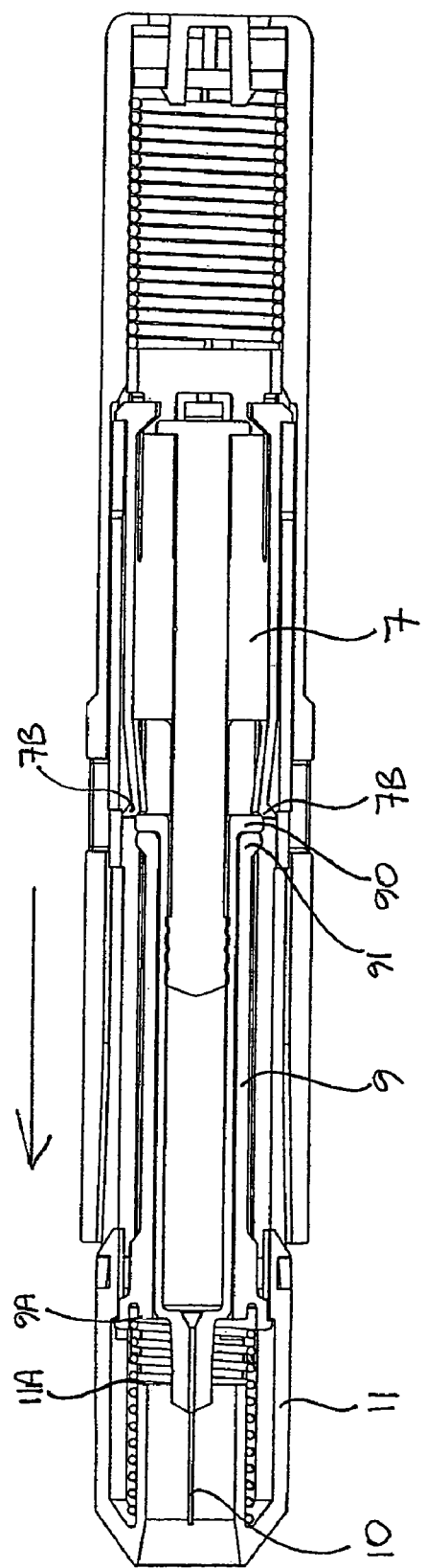
FIG. 3 (PRIOR ART) is a plan view, partly in section of the FIG. 2 device, with the cap and needle cover removed, ready for actuation.
Figure 4:
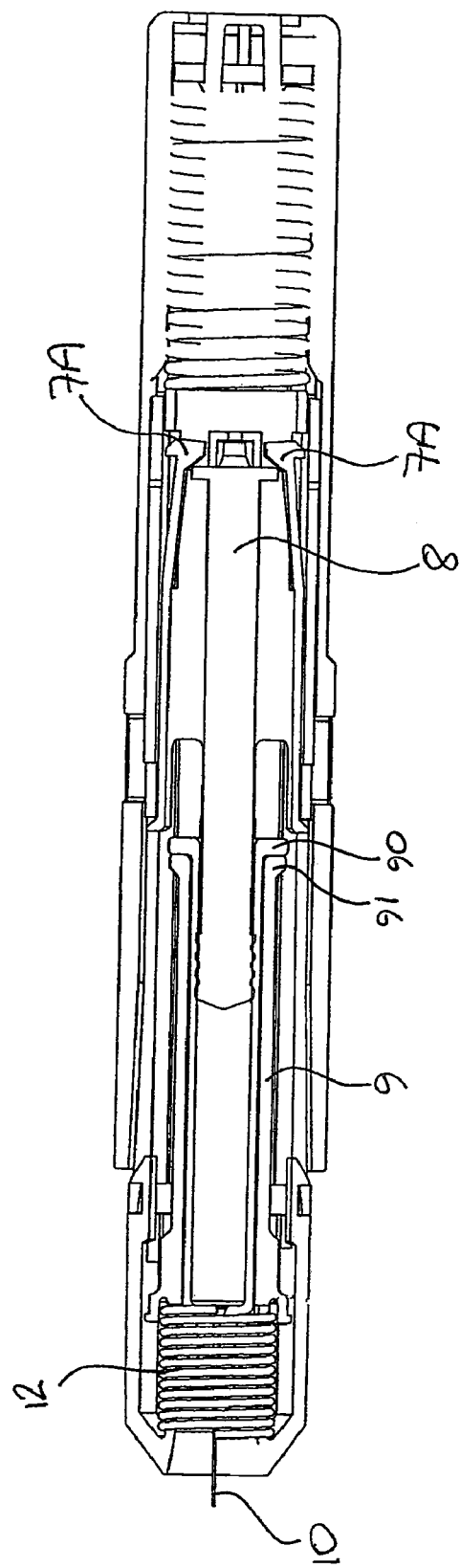
FIG. 4 (PRIOR ART) is a plan view, partly in section of the FIG. 2 device, with the needle exposed, ready for the plunger to be depressed in order to deliver the medicament.
Figure 5:
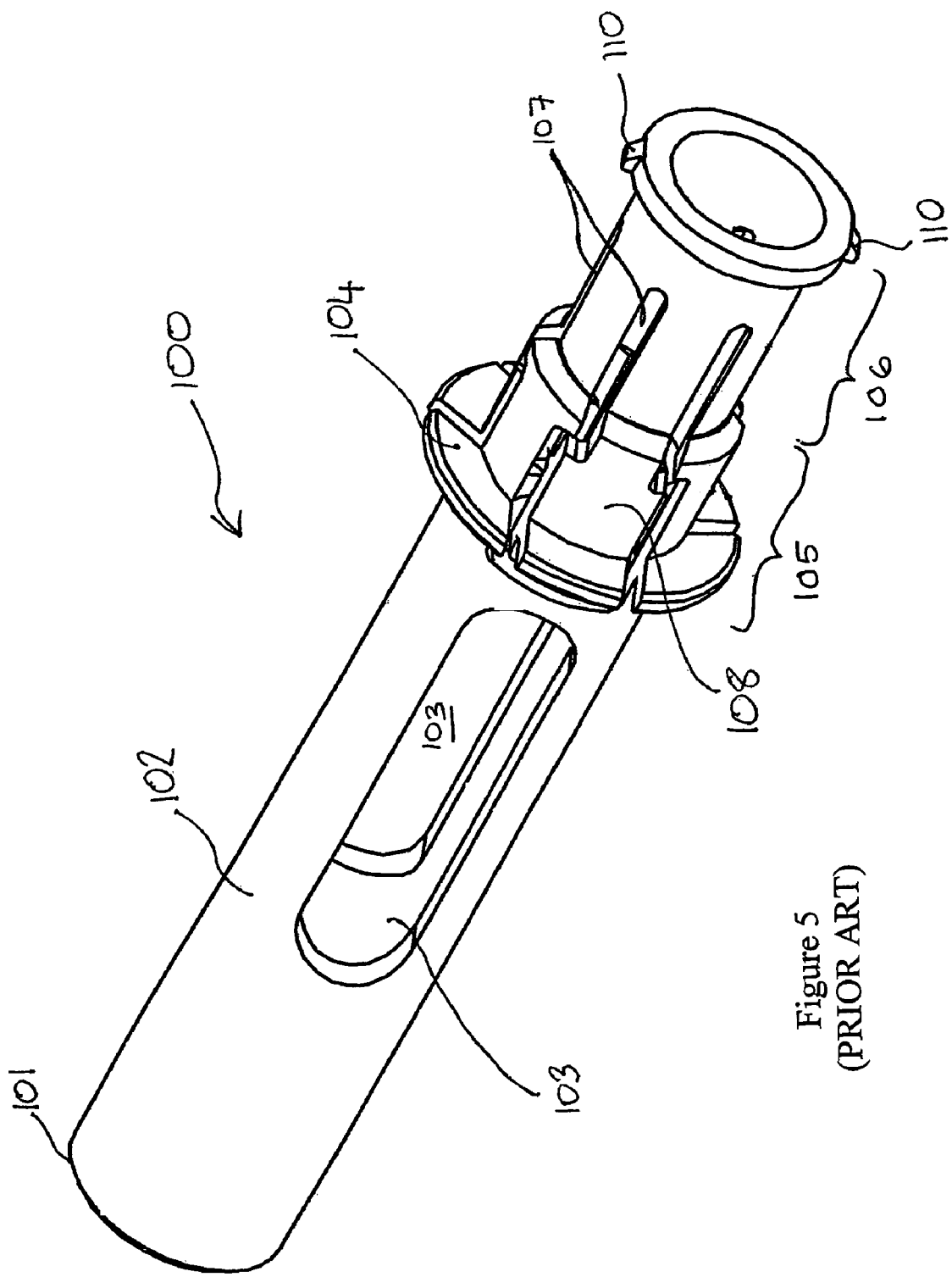
FIG. 5 (PRIOR ART) is a perspective view of an alternative syringe holder from GB0620163.6.
Figure 6:
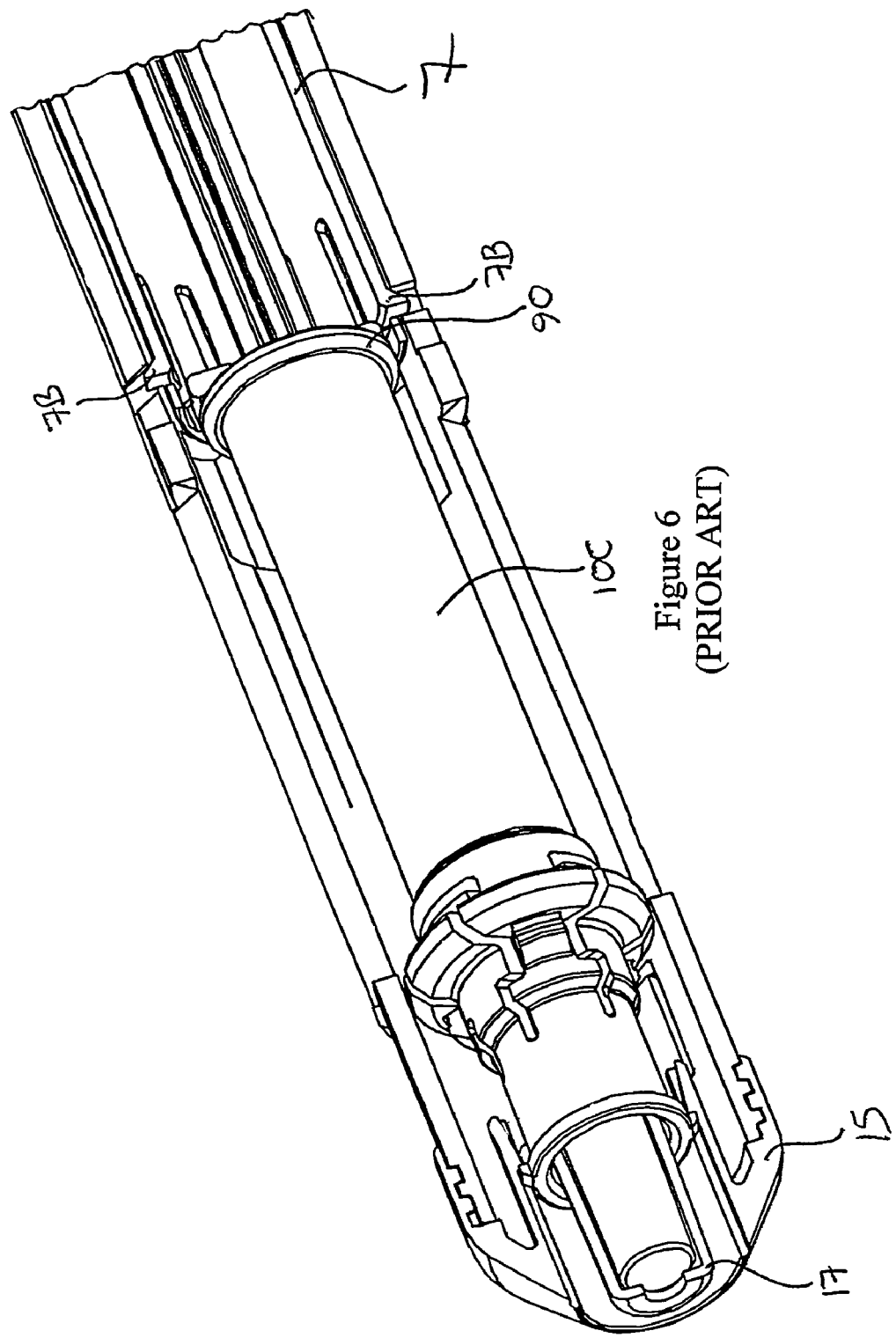
FIG. 6 (PRIOR ART) is a perspective view partly in section showing the inner housing in relation to the syringe holder from GB0620163.6.
Figure 7:
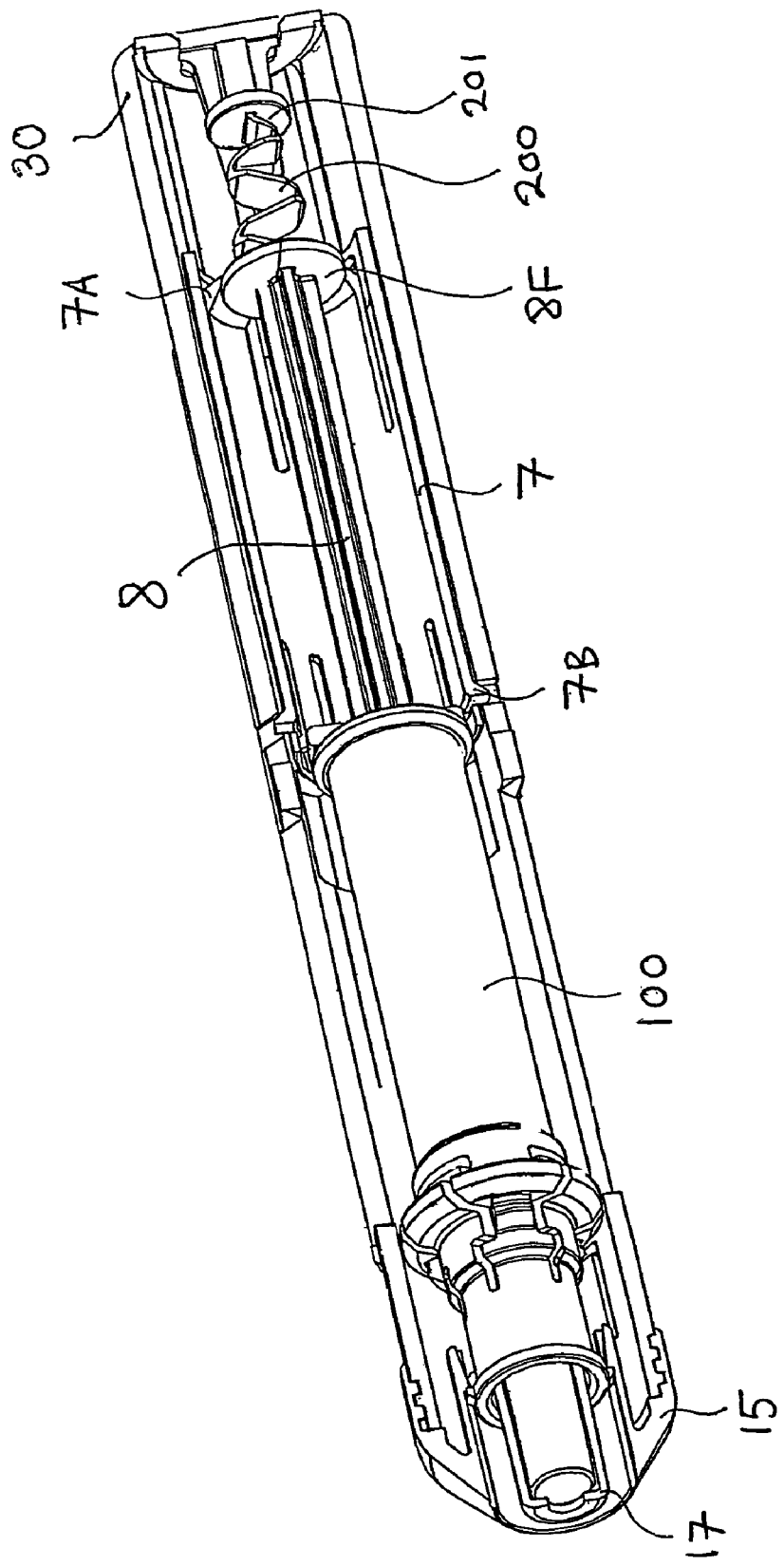
FIG. 7 is a perspective view partly in section showing the inner housing in relation to the syringe holder, the syringe having a modified plunger according to a first embodiment of the invention.

Referring to FIG. 7, a first embodiment of the invention is illustrated. In this embodiment, there is a biasing means in the form of a compression spring 200 between the rear of the outer housing 30 and the flange 8F of the plunger 8. The illustrated spring 200 is integrally formed with the plunger flange 8F, but alternatively, a separate spring could be provided. The spring 200 has a flange 201 at the rear thereof to abut the rear of the outer housing. The spring 200 is a compression spring so that the plunger flange 8F is biased axially forwards so that the syringe as a whole is also biased axially forwards (the biasing force from the spring 200 being transmitted to the rest of the syringe including the barrel via the incompressible liquid medicament therein). This means that the flange 90 of the syringe barrel is always initially located forward of the front tags 7B of the inner housing. The forward axial force provided by the spring 200 is relatively weak and needs only be sufficient to bias the syringe forwards. The force is not sufficient to cause medicament to be ejected from the front of the device, nor is it sufficient to affect the operation of the main energy source (usually a much more powerful spring) which actuates the device when delivery of an injection is required.

Using this modified plunger, the performance of the device is improved, as one always knows that the syringe flange's initial axial position is biased forward of the rear tags 7B, avoiding the risk of malfunction.

Figure 8:
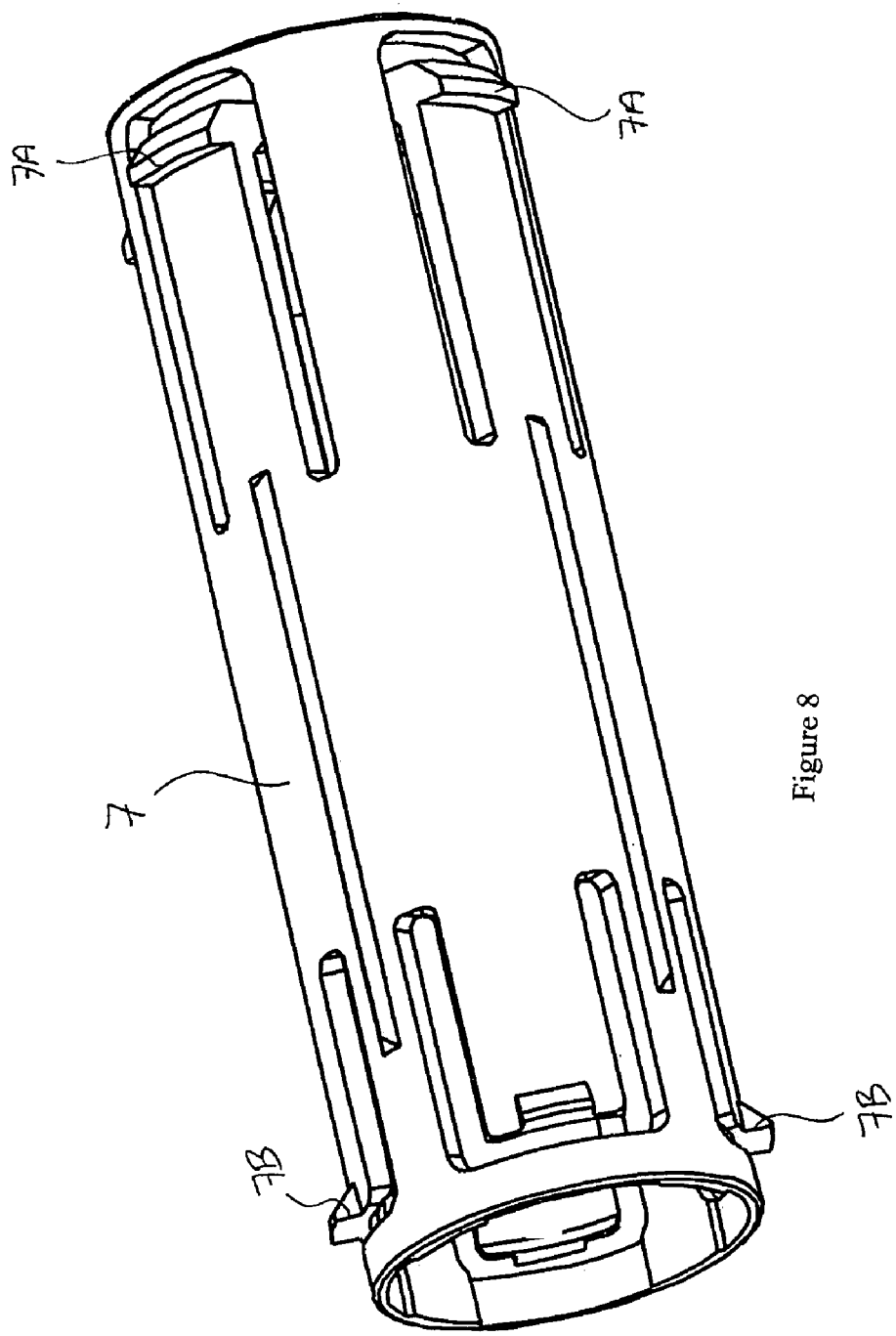
FIG. 8 is a perspective view of a modified inner housing.

Using the modified plunger, the axial position of the plunger is such that it is possible to for the tags 7A, 7B to be stored in their radially-outward position, which is preferable given the above-described tendency for the tags to acquire "memory" of their stored position. In order to avoid the risk of one set of the tags catching in the recesses intended for the other set of tags, the front tags 7B are radially offset from the rear tags 7A, for example by 45°, as illustrated in FIG. 8.

Figures 9, 10:
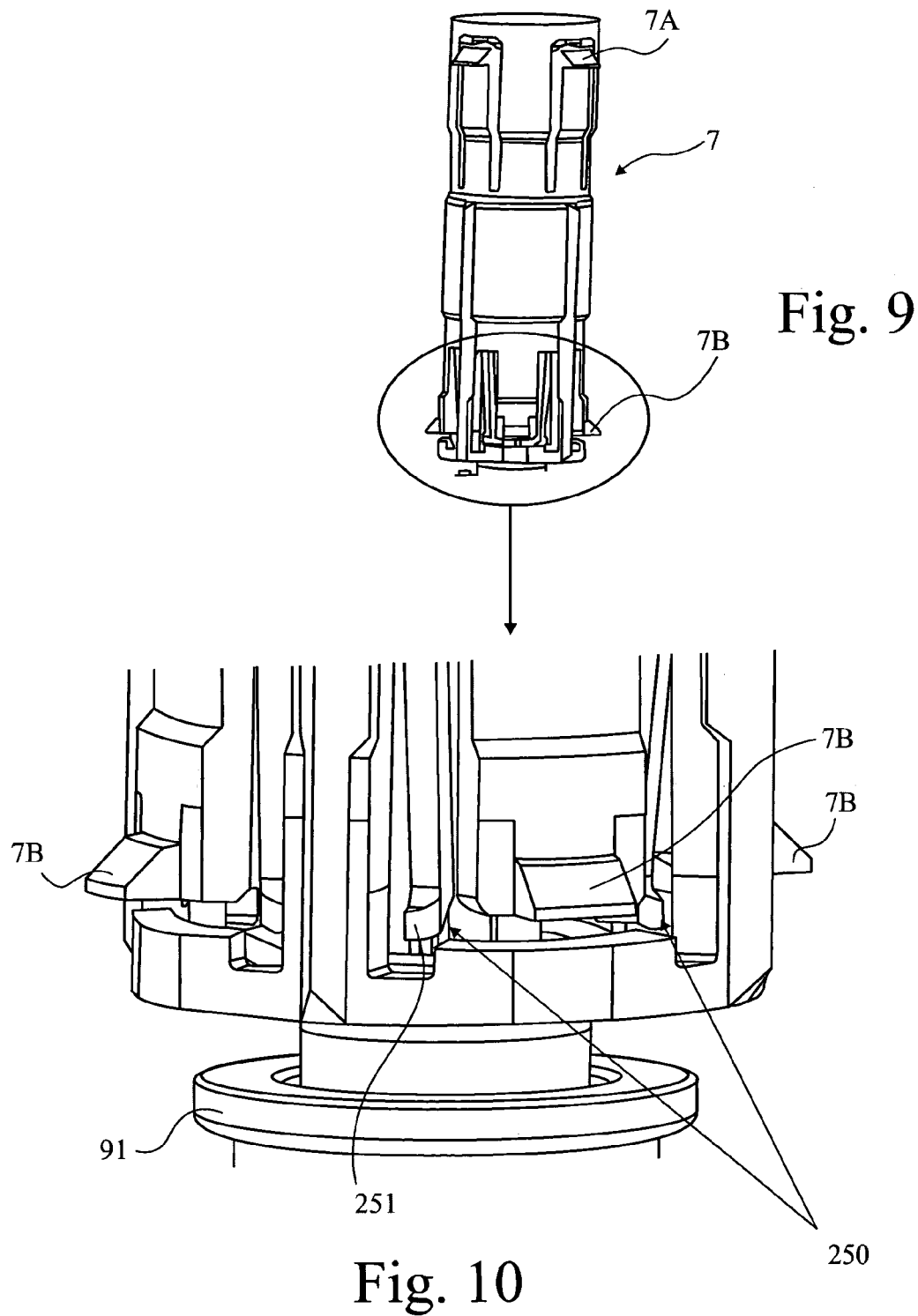
FIG. 9 is a perspective view of a further modified inner housing, embodying a second aspect of the invention.
FIG. 10, drawn to a larger scale, shows further detail of a part of the inner housing of FIG. 9.
Figure 11:
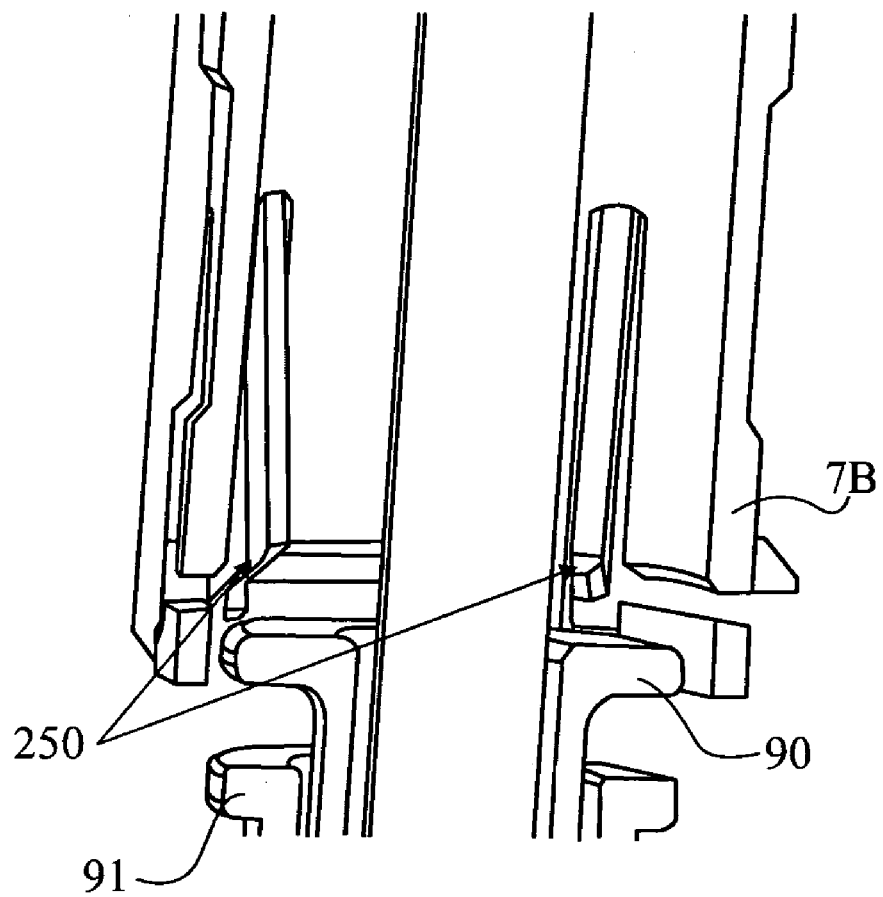
FIG. 11 is a cross-sectional view of part of the inner housing of FIG. 9.

An alternative embodiment of the invention is shown in FIGS. 9-11. In this embodiment, the biasing means are provided as part of a modified inner housing.

Referring to FIG. 9, the inner housing 7 has rear tags 7A and front tags 7B having the same function as described above.

In addition, and as shown best in FIG. 10, the front end of the inner housing is provided with one or more biasing means in the form of radially flexible legs 250. The legs are preferably integrally formed with the inner housing 7. Each flexible leg 250 may have an enlarged head 251.

Normally, before the autoinjector is fired, the legs 250 are flexed radially inwards so that they are in the axial path of the finger flange 90 of the syringe barrel. FIGS. 10 and 11 show the finger flange 90 of the syringe barrel and the barrel seat 91 at the rear of the device's syringe holder. The legs 250 may be moulded so that this is their default position. The legs 250 need not abut the finger flange 90 (although they may do so) but they must at least partially block its rearward axial path. In this way, undesirable rearward axial movement of the finger flange 90 is prevented and the syringe barrel is biased to a position forward of the front tags 7B. Again, the performance of the device is improved, as one always knows that the syringe flange's initial axial position is biased forward of the rear tags 7B, avoiding the risk of malfunction.

The legs 250 of the inner housing 7 are relatively weak and need only to be strong enough to resist the weight of the syringe to prevent undesirable axial movement. They do not impede the firing of the autoinjector to deliver medicament. When the autoinjector is actuated, the inner housing 7 is urged forward by the full force of the main energy source. The legs 250 cannot resist this force and so they are forced radially-outwardly, out of the path of the finger flange 90. Therefore it is possible for the front tags 7B to engage the finger flange 90 in the normal way to move the syringe axially forward enough to move the needle out of the housing into the injection site.

An alternative embodiment of the invention is shown schematically in FIGS. 12-17. In this embodiment, the rear of the plunger 8 is attached to a chamber 300 filled with a shear thickening fluid. A shear thickening fluid is one whose viscosity increases with the rate of shear and is sometimes referred to as a "dilatant" material. The chamber 300 is fixed with respect to the plunger 8.

Figure 12:
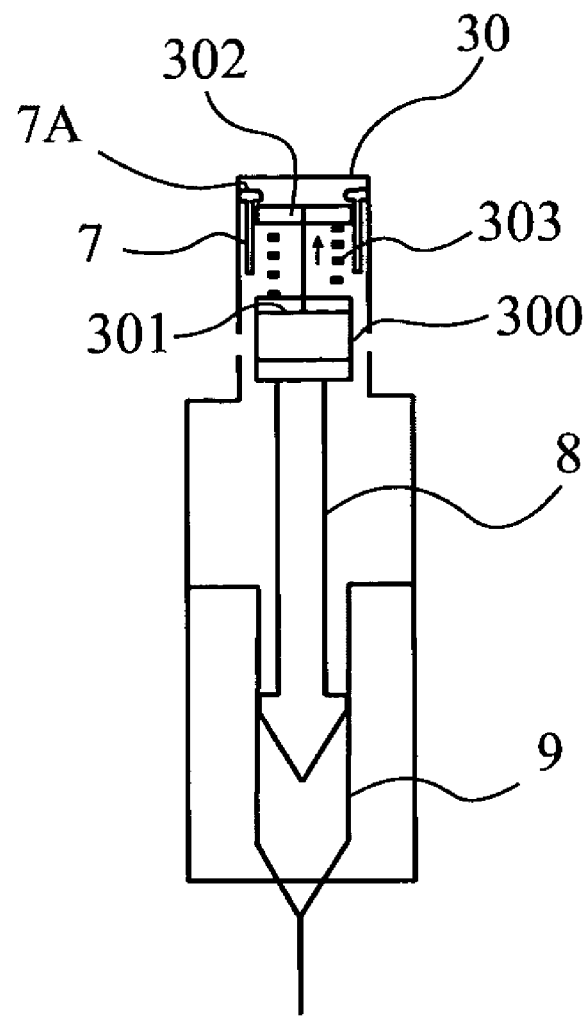
FIGS. 12-17 are schematic cross-sectional views of a second embodiment of the invention, showing various stages of operation of the device.

The chamber 300 contains an axially-moveable piston 301 which does not fill the cross-section of the chamber, so that the shear thickening fluid is able to pass freely around the piston. The piston 301 is attached to and fixed with respect to a rear flange 302. The rear tags 7A of the inner housing engage behind the rear flange 302, in the same way as if the rear flange were the flange of the plunger (8F) in the FIG. 7 embodiment. A compression spring 303 is disposed between the rear flange 302 and the rear surface of the chamber 300, as shown in FIG. 12, so that the rear flange 302 is always biased against the rear tags 7A of the inner housing. The outer housing of the device is labelled as item 30 and the barrel of the syringe is labelled as item 9 in FIG. 12.

The chamber 300 acts as a linear dashpot and, in combination with the spring 303 may be referred to as biasing means.

Figure 13:
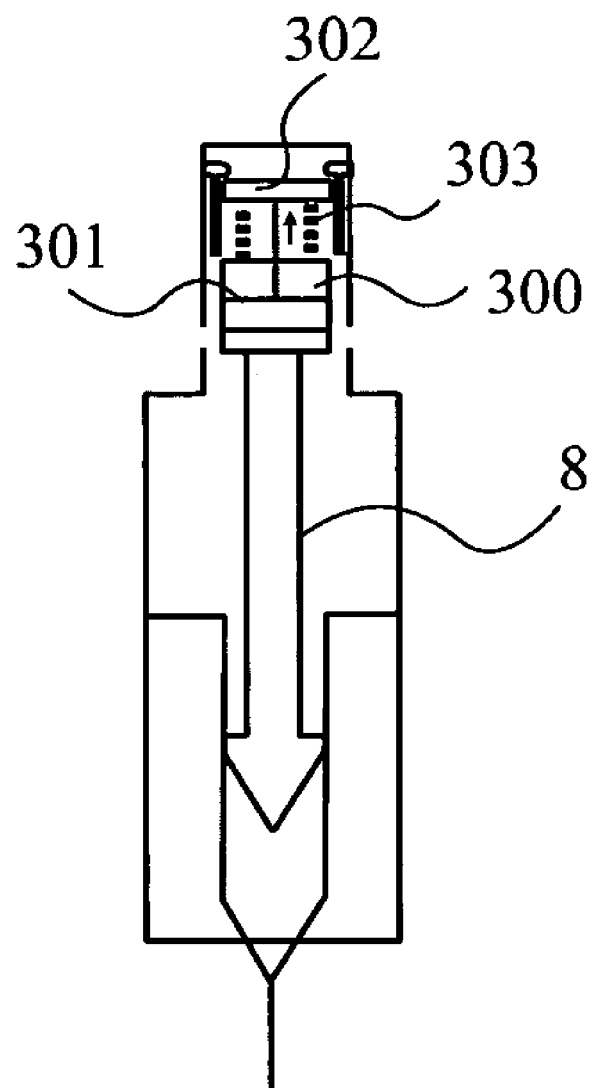

FIG. 13 shows what happens when the plunger 8 moves during storage and/or transportation of the device. For example, the pressure inside the syringe may change if the device is transported by airfreight when any gas bubble inside the syringe may change in volume, causing the plunger 8 to move axially. The axial movement is relatively slow and is not forceful enough to change the viscosity of the shear thickening fluid. Consequently, as the plunger 8 moves rearwardly (upwards as illustrated in FIG. 13) so does the chamber 300. However, the piston 301 does not move rearwardly (as it is attached to the rear flange 302) and so the shear thickening fluid moves around it as the chamber moves rearwardly. The distance between the rear flange 302 and the rear surface of the chamber 300 reduces as the spring 303 is compressed. If the plunger moves forwards, the opposite happens i.e. the distance between the rear flange 302 and the rear surface of the chamber 300 increases. The spring 303 always keeps the rear flange 302 biased against the tags 7A of the inner housing.

Figure 14:
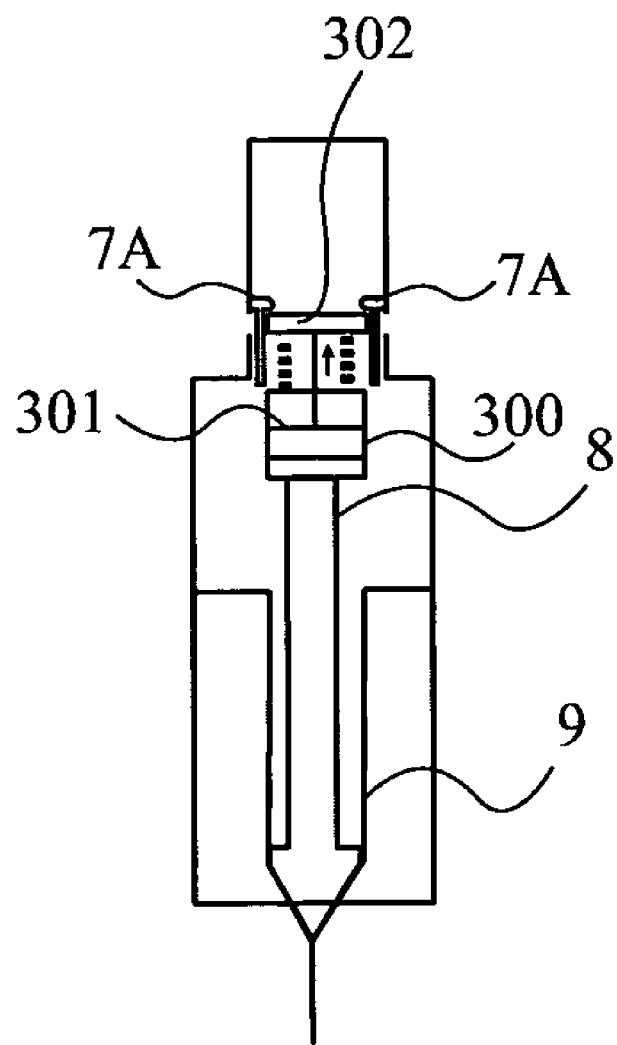

FIG. 14 shows what happens when the device is actuated to deliver an injection. As the inner housing 7 moves forwards with the rear tags 7A engaged behind the rear flange 302, the strong driving force of the device's main energy source causes the viscosity of the shear thickening fluid to change and the fluid thickens. The thick fluid can no longer move freely around the piston 301 and the chamber 300 acts, effectively, as a solid bridge between the rear flange 302 and the plunger 8, so that the plunger 8 is driven into the barrel 9 of the syringe to deliver the medicament.

Figure 15:
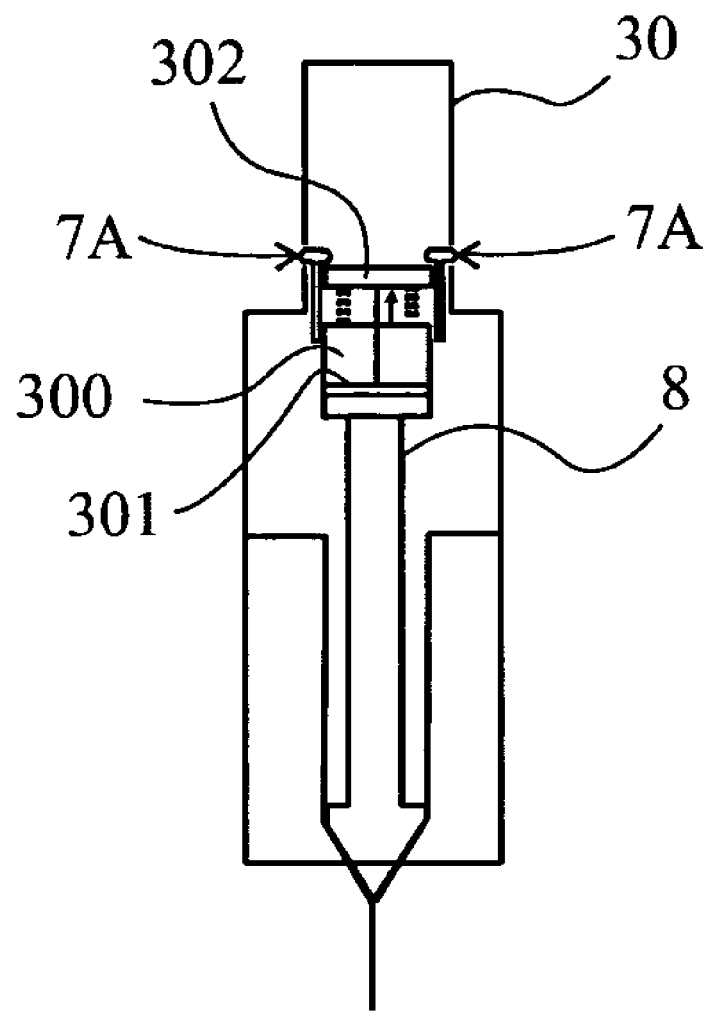

FIG. 15 shows what happens when the dose of medicament has been delivered. When the plunger 8 reaches the end of its forward travel inside the syringe, the piston 301 continues to move forwards, albeit at a reduced speed because the thickened shear thickening fluid is still able to flow to some extent. Therefore the inner housing 7 is able to continue forwards slightly after the full dose of medicament has been delivered. This extra forward movement ensures that the inner housing 7 reaches its desired forward position regardless of its absolute initial axial starting position. This is necessary in order for the rear tags 7A to move radially-outwardly releasing the rear flange 302 as shown in FIG. 16.

Thus, although the rear flange 302 is always initially biased against the rear tags 7A, the shear thickening fluid chamber provides an axial range of possible initial starting points for the plunger 8.

Figure 16:
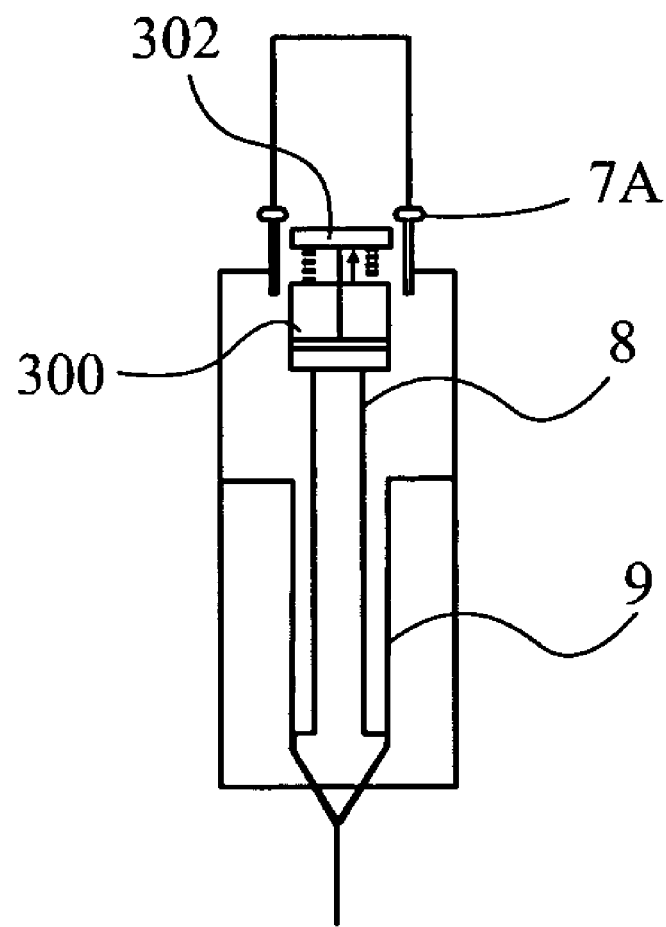
Figure 17:
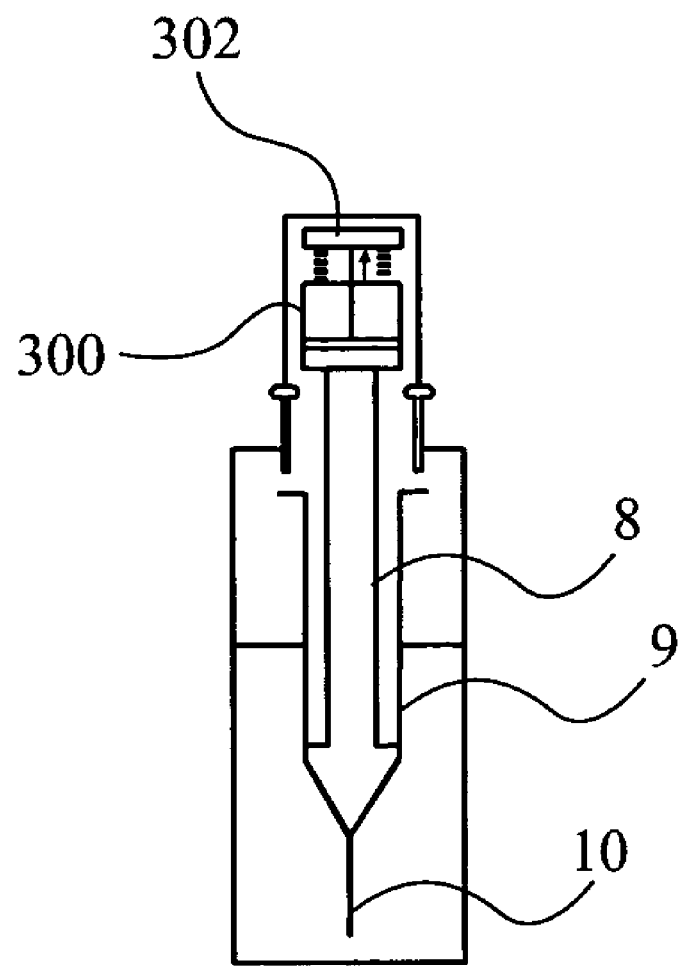

Once the rear tags 7A are fully disengaged from the rear flange, as shown in FIG. 16, the rear flange 302, chamber 300 and plunger 8 are free to move axially rearwardly under the force of a secondary spring at the front of the device (not illustrated). As shown in FIG. 17, the needle 10, syringe barrel 9, plunger 8, chamber 300 and rear flange 302 can all retract into the device so that the needle is fully concealed from the patient's view.

A significant advantage of the chamber of shear thickening fluid is that a precise absolute axial starting point of the plunger is no longer required for proper functioning of the device. The chamber of shear thickening fluid absorbs the effect of minor axial movements of the plunger during storage and transportation. Thus, although the rear flange 302 is always initially biased against the rear tags 7A, the shear thickening fluid chamber provides an axial range of possible initial starting points for the plunger 8. Regardless of the absolute initial starting point for the plunger 8, the shear thickening fluid enables a defined relative axial movement to occur in order to deliver the required dose.

Figure 18:
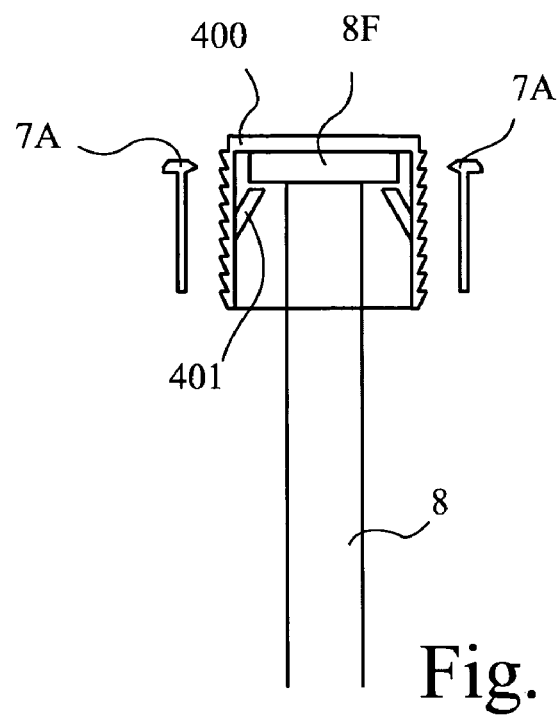
FIG. 18 is a schematic cross-sectional view of the rear part of the plunger having a ratchet cap.

A further improvement is illustrated in FIG. 18. Here, instead of the chamber of shear thickening fluid, a ratchet cap 400 is provided which sites over the rear flange 8F of the plunger 8, locked into place by locking tabs 401. The rear tags 7A of the inner housing can engage anywhere along the ratchet cap 400, depending upon the absolute axial position of the plunger (and consequently the ratchet cap attached thereto). This also effectively provides a plurality of axial starting positions for the plunger for which the device will work to deliver the required dose of medicament. The ratchet cap embodiment could be used in combination with the modified plunger rod of FIG. 7. Other alternatives, instead of the illustrated ratchet cap, may be used to provide the range of axial starting positions for the plunger, for example a differently shaped component intermediate the inner housing tags and plunger. Alternatively, the ratchet cap or equivalent component could be an integral part of a modified plunger, for example a plunger having a plurality of annular ribs.

Figure 19:
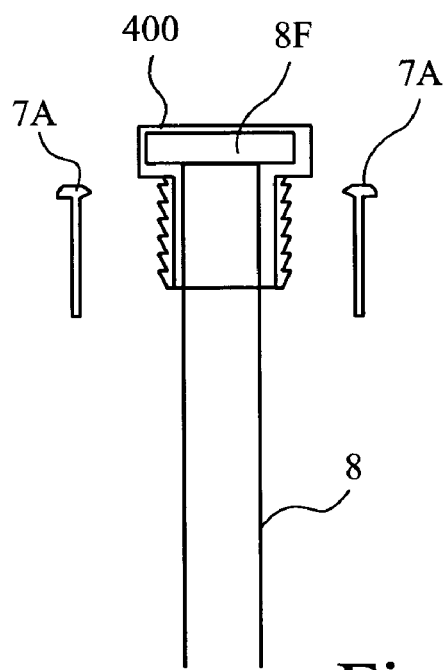
FIG. 19 is a schematic cross-sectional view of the rear part of the plunger having an alternative embodiment of the ratchet cap.

The diameter of the inner housing 7 may need to be increased slightly to accommodate the extra diameter of the ratchet cap. Alternatively, the ratchet cap could be shaped as shown in FIG. 19 so that the diameter of the device does not need to be increased. This embodiment has the advantage that the overall length of the device could be reduced with the rear flange positioned further back in the device, inside the main spring (the device's main energy source).

The reader's attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. An autoinjector comprising an outer housing in which is mounted a syringe, comprising:
   a barrel for holding a volume of medicament;
   a needle at one end of the barrel; and
   a plunger axially-moveable in the barrel;
the autoinjector further comprising an inner housing intermediate the outer housing and the syringe and an energy source in communication with said inner housing,
wherein the inner housing comprises one or more radially-flexible tags, wherein the one or more radially-flexible tags are moveable radially into and out of communication with the plunger,
wherein the inner housing is moveable by the energy source between three positions, namely
   a first position in which the inner housing is in communication with the barrel such that, in use, the plunger and barrel are moveable axially so as to move at least part of said needle out of the outer housing;
   a second position in which the inner housing is in communication with the plunger but not the barrel such that, in use, said plunger is moveable axially into said barrel so as to expel medicament through the needle; and
   a third position in which the inner housing is in communication with neither the plunger nor the barrel such that, in use, the plunger and barrel are able to retract in order to retract the needle into the outer housing, characterised in that the autoinjector further comprises means associated with a rear flange of said plunger providing a plurality of axial positions at which it is possible for said inner housing to engage said plunger in said second position.

2. The autoinjector of claim 1, wherein said means comprises a chamber containing a piston in a shear thickening fluid which, upon activation of said energy source, is capable of transmitting forward axial force from said energy source to the plunger, and a compression spring held between the outer housing and said piston.

3. The autoinjector of claim 1, wherein said means comprises a ratchet cap intermediate said inner housing and said plunger.

4. The autoinjector of claim 1, further including biasing means for axially biasing the barrel, before activation of the energy source, to a position forward of the part of the inner housing which acts on the barrel in said first position.

5. The autoinjector of claim 1, further comprising syringe support means for supporting the barrel at an axial location at or forward of a forwardmost position of the plunger and having a reaction surface for the syringe, whereby in use said reaction surface provides an axial compressive force on said barrel when a forward axial force is applied to the plunger.

6. The autoinjector of claim 1, wherein said autoinjector is a single-use autoinjector.

7. The autoinjector of claim 1, wherein said energy source is capable of moving said plunger axially in the barrel to deliver an injection in less than 30 seconds.

8. The autoinjector of claim 1, wherein one or more of said tags is located at the end of a resiliently flexible leg.

9. The autoinjector of claim 1, wherein one or more of said tags are situated at the rear end of the inner housing.

10. An autoinjector comprising an outer housing in which is mounted a syringe, comprising:
   a barrel for holding a volume of medicament;
   a needle at one end of the barrel; and
   a plunger axially-moveable in the barrel;
the autoinjector further comprising an inner housing intermediate the outer housing and the syringe and an energy source in communication with said inner housing,
   wherein the inner housing comprises one or more radially-flexible tags, wherein one or more of the radially flexible tags are situated at the forward end of the inner housing and are moveable radially into and out of communication with the barrel, wherein the inner housing is moveable by the energy source between three positions, namely a first position in which the inner housing is in communication with the barrel such that, in use, the plunger and barrel are moveable axially so as to move at least part of said needle out of the outer housing;

a second position in which the inner housing is in communication with the plunger but not the barrel such that, in use, said plunger is moveable axially into said barrel so as to expel medicament through the needle; and a third position in which the inner housing is in communication with neither the plunger nor the barrel such that, in use, the plunger and barrel are able to retract in order to retract the needle into the outer housing, characterised in that the autoinjector further comprises means associated with a rear flange of said plunger providing a plurality of axial positions at which it is possible for said inner housing to engage said plunger in said second position.

11. The autoinjector as claimed in claim 1, wherein said tags are stored in their relaxed, radially-outward, condition, before initiating an injection.

12. The autoinjector as claimed in claim 10, wherein one or more of said tags are situated at the rear end of the inner housing and are moveable radially into and out of communication with the plunger, and the one or more tags situated at the rear of the inner housing are radially offset from the one or more tags situated at the forward end of the inner housing, preferably by 45 degrees.

13. The autoinjector of claim 1, wherein the syringe is axially moveable in said housing and is biased so that the needle is normally wholly inside said housing, wherein before injection the syringe is movable axially so as to move at least a part of said needle out of the housing, and wherein after injection, the syringe is able to retract in order to retract said part of said needle into the housing.

14. The autoinjector of claim 5, wherein, in use, said reaction surface provides an axial compressive force to the front shoulder or the front cone of the syringe barrel.

15. The autoinjector of claim 5, wherein said syringe support means includes one or more inwardly-directed protrusions forming said reaction surface.

16. The autoinjector of claim 15, wherein said inwardly-directed protrusions are on the end of one or more radially-flexible fingers.

17. The autoinjector of claim 15, wherein, when the device is fully assembled ready for use, said inwardly-directed protrusions are axially located between a needle cover and the front shoulder of the syringe barrel.

18. The autoinjector of claim 5, wherein the finger flange of the syringe barrel does not contact the syringe support means during delivery of the medicament.

19. The autoinjector of claim 15, wherein said radially-flexible fingers can flex sufficiently outwardly to allow a needle cover or the like of larger diameter than the internal diameter between said radially-flexible fingers to pass thereby during assembly of a syringe into said autoinjector.

* * * * *